US00PP27005P2

(12) United States Plant Patent
Koppe

(10) Patent No.: US PP27,005 P2
(45) Date of Patent: Aug. 2, 2016

(54) ***BEGONIA* PLANT NAMED 'KRVALPI01'**

(50) Latin Name: *Begonia×hiemalis*
Varietal Denomination: KRVALPI01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 92 days.

(21) Appl. No.: 14/121,547

(22) Filed: Sep. 17, 2014

(51) Int. Cl.
*A01H 5/02* (2006.01)

(52) U.S. Cl.
USPC ..... Plt./344

(58) Field of Classification Search
USPC ..... Plt./344
See application file for complete search history.

(56) References Cited

PUBLICATIONS

PLUTO: Plant Variety Database, UPOV, QZ PBR 39378, published Feb. 15, 2014.*

* cited by examiner

*Primary Examiner* — Anne Grunberg
(74) *Attorney, Agent, or Firm* — C. A. Whealy

(57) ABSTRACT

A new and distinct cultivar of *Begonia* plant named 'KRVALPI01' characterized by its upright, outwardly spreading and mounded plant habit; moderately vigorous growth habit; freely branching habit; dark green-colored leaves; numerous large double reddish pink-colored flowers with bright yellow-colored centers; and excellent postproduction longevity.

2 Drawing Sheets

Botanical designation: *Begonia×hiemalis.*
Cultivar denomination: 'KRVALPI01'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'KRVALPI01'.

The new *Begonia* plant is a product of a planned breeding program conducted by the Inventor in Ermelo, The Netherlands. The objective of the breeding program is to create new types of *Begonia* plants with unique and attractive flower forms.

The new *Begonia* plant originated from a cross-pollination made by the Inventor in Ermelo, The Netherlands in January, 2009 of a proprietary selection of *Begonia×tuberhybrida* identified as code number KV07K1338-09, not patented, as the female, or seed, parent with an unnamed proprietary selection of *Begonia socotrana*, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in September, 2009.

Asexual reproduction of the new *Begonia* plant by vegetative cuttings taken in a controlled greenhouse environment in Ermelo, The Netherlands since January, 2010 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRVALPI01'. These characteristics in combination distinguish 'KRVALPI01' as a new and distinct *Begonia* plant:

1. Upright, outwardly spreading and mounded plant habit.
2. Moderately vigorous growth habit.
3. Freely branching habit.
4. Dark green-colored leaves.
5. Numerous large double reddish pink-colored flowers with bright yellow-colored centers.
6. Excellent postproduction longevity.

Plants of the new *Begonia* differ primarily from plants of the female parent selection in flower color as plants of the female parent selection have orange-colored flowers.

Plants of the new *Begonia* differ primarily from plants of the male parent selection in flower color as plants of the male parent selection have pink-colored flowers.

Plants of the new *Begonia* can also be compared to plants of *Begonia×hiemalis* 'Dark Netja', not patented. In side-by-side comparisons conducted in Ermelo, The Netherlands, plants of the new *Begonia* differed primarily from plants of 'Dark Netja' in flower type and color as plants of 'Dark Netja' had semi-double pink-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'KRVALPI01' grown in a container.

The photograph on the second sheet are close up views of the upper and lower surfaces of typical leaves (right) and upper, lateral and lower surfaces of developing and open flowers of 'KRVALPI01' (left).

DETAILED BOTANICAL DESCRIPTION

The aforementioned photographs and following observations and measurements describe plants grown during the spring and early summer in 13-cm containers in a shaded glass-covered greenhouse in Ermelo, The Netherlands and under cultural practices typical of commercial *Begonia* production. During the production of the plants, day temperatures averaged 20° C. and night temperatures averaged 18° C. Plants were pinched one time and were twelve weeks old when the photographs and description were taken. In the following description, color references are made to The Royal Horticultural Society Colour Chart, 2007 Edition, except where general terms of ordinary dictionary significance are used.

Botanical classification: *Begonia×hiemalis* 'KRVALPI01'.

Commercial classification: Elatior *Begonia*.

Parentage:

*Female, or seed, parent*.—Proprietary selection of *Begonia×tuberhybrida* identified as code number KV07K1338-09, not patented.

*Male, or pollen, parent*.—Unnamed proprietary selection of *Begonia socotrana*, not patented.

Propagation:

*Type*.—By terminal vegetative cuttings.

*Time to initiate roots*.—About 20 days at temperatures about 20° C.

*Time to produce a rooted young plant*.—About five weeks at temperatures about 20° C.

*Root description*.—Fine, fibrous; white to orange brown in color.

*Rooting habit*.—Freely branching; medium density; plants of the new *Begonia* have not been observed to form tubers.

Plant description:

*Plant habit and form*.—Upright, outwardly spreading and mounded plant habit; overall plant shape broadly upright and globular; flowers held above and beyond the foliar plane.

*Growth habit*.—Moderately vigorous growth habit and moderate growth rate; suitable for 12-cm and larger containers; under optimal environmental and cultural conditions, usually about ten weeks are required to produce proportional 13-cm potted plants from cuttings; vegetative shoots are formed at basal nodes and flowering shoots are formed at upper nodes.

*Branching habit*.—Freely branching habit; when pinched, about seven lateral branches develop.

*Plant height*.—About 26.2 cm.

*Plant width*.—About 33.5 cm.

*Lateral branches*.—Length: About 15 cm. Diameter: About 1.1 cm. Internode length: About 2.6 cm. Angle: About 45° from vertical. Texture: Smooth, sparsely pubescent. Color, developing: Close to 144A to 144B. Color, fully developed: Close to 146A to 146B.

*Leaves*.—Arrangement: Alternate; simple. Length: About 14.1 cm. Width: About 9.4 cm. Shape: Ovate to broadly ovate. Apex: Acute. Base: Oblique. Margin: Bi-serrate; laciniate. Texture, upper surface: Smooth, glabrous; velvety. Texture, lower surface: Sparse pubescence along veins. Venation pattern: Palmate. Color: Developing leaves, upper surface: Close to 141B slightly tinged with close to N199A. Developing leaves, lower surface: Close to 144B tinged with close to 176B. Fully expanded leaves, upper surface: Darker than between 147A and N189A; venation, close to 146A to 146B. Fully expanded leaves, lower surface: Close to 147B to 147C heavily tinged with close to 178A; venation, close to 146B. Petioles: Length: About 6.4 cm. Diameter: About 6 mm. Texture, upper and lower surfaces: Sparsely to moderately pubescent. Color, upper surface: Close to 152A slightly tinged with close to 176B; distally, close to 178A to 178B. Color, lower surface: Close to 152A slightly tinged with close to 176B. Stipules: Length: About 1.2 cm. Width: About 1 cm. Shape: Broadly ovate. Margin: Entire. Texture, upper and lower surfaces: Smooth, glabrous. Color, upper and lower surfaces: Close to 145B; venation, close to 145A.

Flower description:

*Flower form and flowering habit*.—Large double rotate flowers arranged in axillary compound cymes; usually about 5 to 14 flowers per cyme, numerous cymes in flower simultaneously and about 330 flowers developing per plant; flowers face upright to outwardly and are positioned above and beyond the foliar plane.

*Natural flowering season*.—Plants begin flowering about six weeks after pinching; plants flower continuously year round regardless of nyctoperiod, however plants are more freely flowering from spring until autumn in The Netherlands.

*Flower longevity*.—Individual flowers last about ten days on the plant; flowers not persistent; flowering plants have excellent postproduction longevity and typical maintain good substance for about five weeks under interior conditions.

*Fragrance*.—None detected.

*Inflorescence height*.—About 15 cm.

*Inflorescence diameter*.—About 10.6 cm.

*Flower buds*.—Length: About 2.2 cm. Diameter: Ranging from about 9 mm to 17 mm. Shape: Obovate to broadly oblong, flattened. Color: Close to 51B.

*Flowers*.—Shape: Rotate; double. Diameter: About 5.9 cm. Depth (height): About 1.2 cm.

*Tepals*.—Quantity per flower: About four arranged in a single whorl. Length: About 2.9 cm. Width: About 2.9 cm. Shape: Roughly orbicular. Apex: Rounded. Margin: Entire. Texture, upper surface: Smooth, glabrous; velvety. Texture, lower surface: Smooth, glabrous; slightly velvety. Color: When opening, upper surface: Close to 52A; towards the base, close to 52B. When opening, lower surface: Close to 48C; towards the margins, close to 50B. Fully opened, upper surface: Close to 52A; towards the base, close to 54B; color does not change with development. Fully opened, lower surface: Close to 36A; towards the margins, close to 50C; color does not change with development.

*Tepaloids*.—Quantity per flower: About 40 arranged in numerous whorls. Length: About 1.5 cm. Width: About 1 cm. Shape: Obovate. Apex: Rounded. Margin: Entire. Texture, upper surface: Smooth, glabrous; velvety. Texture, lower surface: Smooth, glabrous; slightly velvety. Color, outer tepaloids: When opening, upper surface: Close to 52A; towards the base, close to 52B. When opening, lower surface: Close to 48C; towards the margins, close to 50B. Fully opened, upper surface: Close to 52A; towards the base, close to 54B; color does not change with development. Fully opened, lower surface: Close to 36A; towards the margins, close to 50C; color does not change with development. Color, inner tepaloids: When opening, upper surface: Close to 6A to 6B. When opening, lower surface: Close to 5B and 6C. Fully opened, upper surface: Close to between 4B and 5C; color does not change with development. Fully opened, lower surface: Close to 4C to 4D; color does not change with development.

*Peduncles*.—Length: About 11.7 cm. Diameter: About 4 mm. Angle: About 40° from lateral branch axis. Texture: Smooth, glabrous. Color: Close to 144A.

*Pedicels*.—Length: About 3.2 cm. Diameter: About 2 mm. Angle: About 30° from peduncle axis. Texture: Smooth, glabrous. Color: Close to 152B.

*Reproductive organs*.—Stamens: None observed. Pistils: None observed.

*Seeds and fruits*.—Seed and fruit development have not been observed on plants of the new *Begonia*.

Disease & pest resistance: Resistance to pathogens and pests common to *Begonia* has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'KRVALPI01' as illustrated and described.

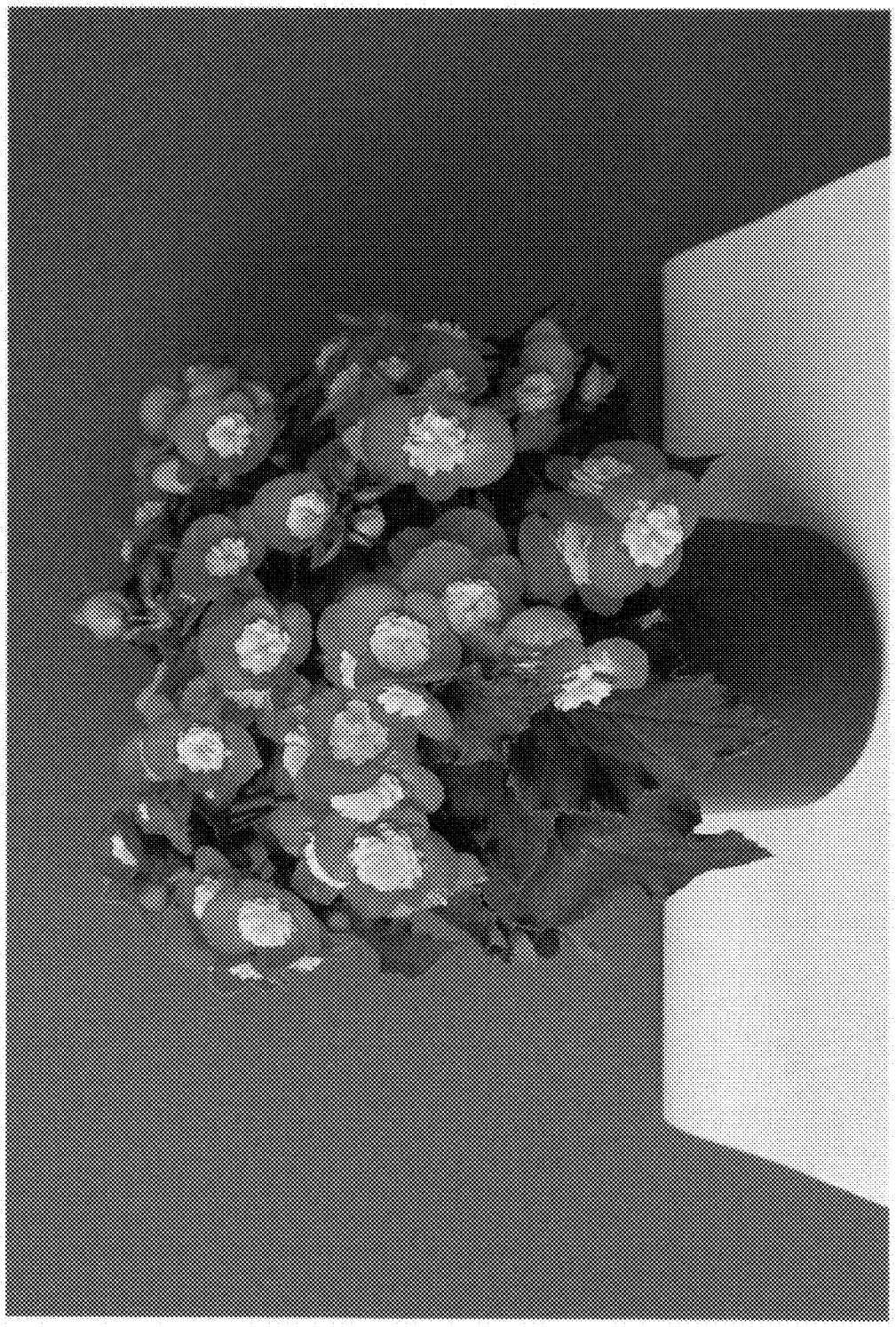

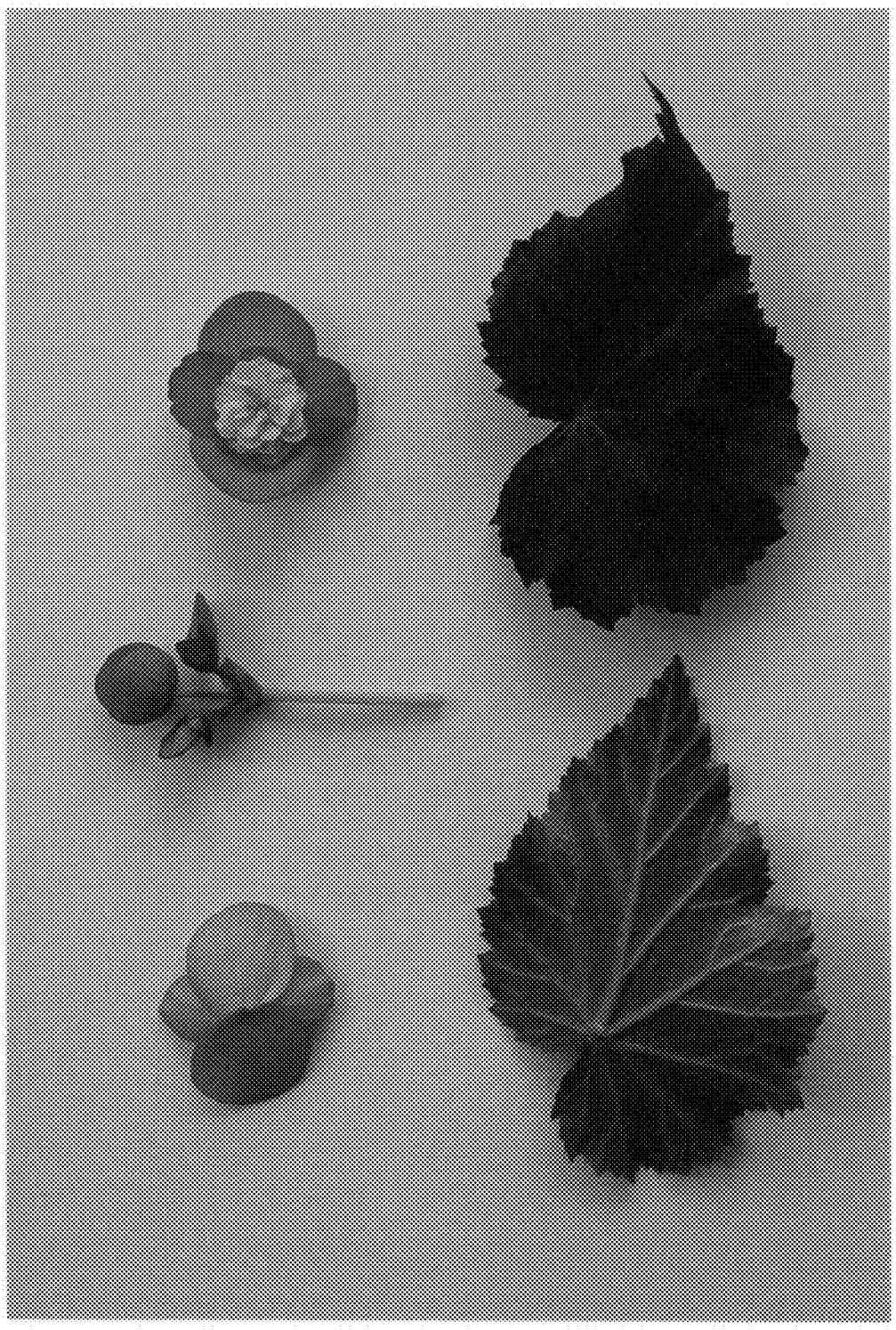

* * * * *